(12) United States Patent
Cox

(10) Patent No.: US 6,994,111 B2
(45) Date of Patent: Feb. 7, 2006

(54) TOROIDAL VESSEL FOR UNIFORM, PLUG-FLOW FLUID DISTRIBUTION APPLICATIONS

(75) Inventor: John R. Cox, Twin Falls, ID (US)

(73) Assignee: Amalgamated Research, Inc., Twin Falls, ID (US)

( * ) Notice: Subject to any disclaimer, the term of this patent is extended or adjusted under 35 U.S.C. 154(b) by 0 days.

(21) Appl. No.: 10/327,390

(22) Filed: Dec. 20, 2002

(65) Prior Publication Data

US 2003/0132145 A1    Jul. 17, 2003

Related U.S. Application Data

(60) Provisional application No. 60/342,985, filed on Dec. 21, 2001.

(51) Int. Cl.
*E03B 11/00* (2006.01)
(52) U.S. Cl. .................................. 137/561 A; 137/592
(58) Field of Classification Search ............ 137/561 A, 137/592
See application file for complete search history.

(56) References Cited

U.S. PATENT DOCUMENTS

| | | | |
|---|---|---|---|
| 4,035,301 A | | 7/1977 | Armstrong |
| 4,299,553 A | * | 11/1981 | Swaroop ...................... 425/572 |
| 4,505,297 A | * | 3/1985 | Leech et al. ............ 137/561 A |
| 4,786,297 A | | 11/1988 | Gethke et al. |
| 5,010,910 A | * | 4/1991 | Hickey .......................... 137/1 |
| 5,040,558 A | * | 8/1991 | Hickey et al. .................. 137/1 |
| 5,181,537 A | * | 1/1993 | Powers .................... 137/561 A |
| 5,524,822 A | | 6/1996 | Simmons |
| 5,653,806 A | | 8/1997 | Van Buskirk |
| 5,884,658 A | | 3/1999 | Cameron |

\* cited by examiner

*Primary Examiner*—A. Michael Chambers
(74) *Attorney, Agent, or Firm*—Traskbritt, P.C.

(57) ABSTRACT

The present invention is an improved vessel body for use in uniform plug-flow fluid applications, such as chromatography and adsorption bed processes. The improved vessel is toroidal shaped and allows for a simpler distribution and collection system, which is likewise claimed.

5 Claims, 5 Drawing Sheets

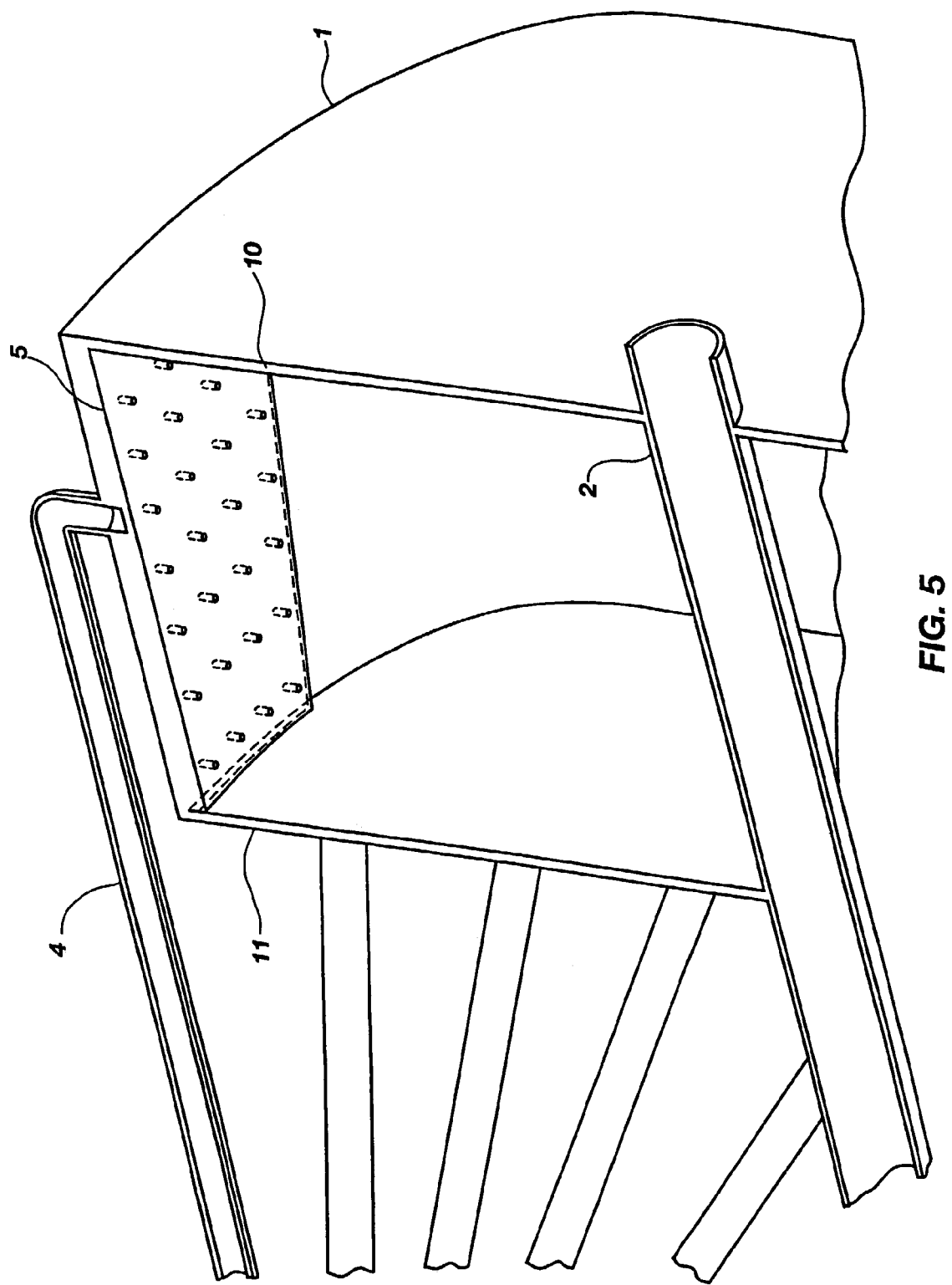

TOROIDAL VESSEL FOR UNIFORM, PLUG-FLOW FLUID DISTRIBUTION APPLICATIONS

CROSS-REFERENCE TO RELATED APPLICATION

This application claims the benefit of U.S. Provisional Application No. 60/342,985, filed Dec. 21, 2001.

BACKGROUND OF THE INVENTION

1. Field of the Invention

The present invention relates to vessels used in applications requiring uniform fluid collection and distribution and more particularly relates to a toroidal vessel for use in such applications.

2. State of the Art

Many processes, such as chromatography, ion exchange, adsorption bed processes and reactor vessel processes, require a uniform, homogenous contact of various fluids with a medium. The contact is usually accomplished in enclosed vessels, or cells, which have been filled with a bed of the needed medium. Since most of the applications require sharp fluid interfaces, the bed depth must be constant and this requirement results in vessels having flat tops and bottoms.

In most cases, the vessels operate with some degree of pressure. Most vessels are shaped cylindrically, with reinforced flat tops and bottoms, to easier hold the pressure. Flat tops and bottoms are often reinforced with curved pressure heads; this also has the disadvantage of increasing the difficulty of routing fluid conduits to the flat surface.

Prior solutions to balancing the need for uniform distribution and collection with a vessel built to withstand pressure have resulted in improved manifolds and vessels having many independent conduits and plenums for distribution and collection of the fluid. U.S. Pat Nos. 4,99,102 and 5,354,460, both of which are herein incorporated by reference, are examples of solutions that provide uniform plug-flow distribution over a wide flow range at a low-pressure drop. The present invention provides the possibility of simpler fluid transport designs utilizing the principles of these patents.

BRIEF SUMMARY OF THE INVENTION

The present invention provides a new design of vessel, allowing for a simpler distribution and collection system. In essence, the vessel body is constructed in the shape of a toroid. A toroid is formed by rotating a closed geometric shape around an axis in the same plane as the shape, but not intersecting the shape. The most common toroidal shape is a circle, creating a doughnut shape when rotated about the axis. The preferred shape for the present invention is a rectangular toroid, thus providing the flat bottoms and tops desired in many applications. A system is provided, wherein two plenums are located axially within the toroid, one for collection, one for distribution. Each plenum is connected to the toroidal vessel by a plurality of conduits extending radially therefrom and into the vessel, said conduits opening into the vessel and in open fluid communication with the plenums. Each plenum is also in open fluid communication with one other conduit, providing intake/outflow to/from the vessel.

The construction of a toroidal vessel allows for numerous advantages over the prior art. First, the distribution and collection manifolds may be located within the void formed by the toroid and both may be symmetrical due to their location. The symmetry provides greater uniformity to fluid flow with a simpler construction as all collection and distribution conduits are identical or at least have identical hydraulic paths. The inner wall of the toroidal body provides more support than compared to a cylindrical vessel, and the span for flat tops and bottoms is reduced, thereby reducing exponentially the bending moments caused by operating pressures. The construction also has a smaller lateral distance between the walls, thereby reducing internal volume as compared to a cylinder and correspondingly reducing material needed to fill the vessel. When using a rectangular toroid, the preferred embodiment, distribution conduits may be kept external to the body, providing unobstructed, flat internal surfaces. The void allows for easier access to internal manifold components, thus allowing for tighter arrangements of multiple vessels.

BRIEF DESCRIPTION OF THE SEVERAL VIEWS OF THE DRAWINGS

FIG. 5 is a perspective section of the invention, focusing on an upper corner of the invention.

DETAILED DESCRIPTION OF THE INVENTION

Figure 1:
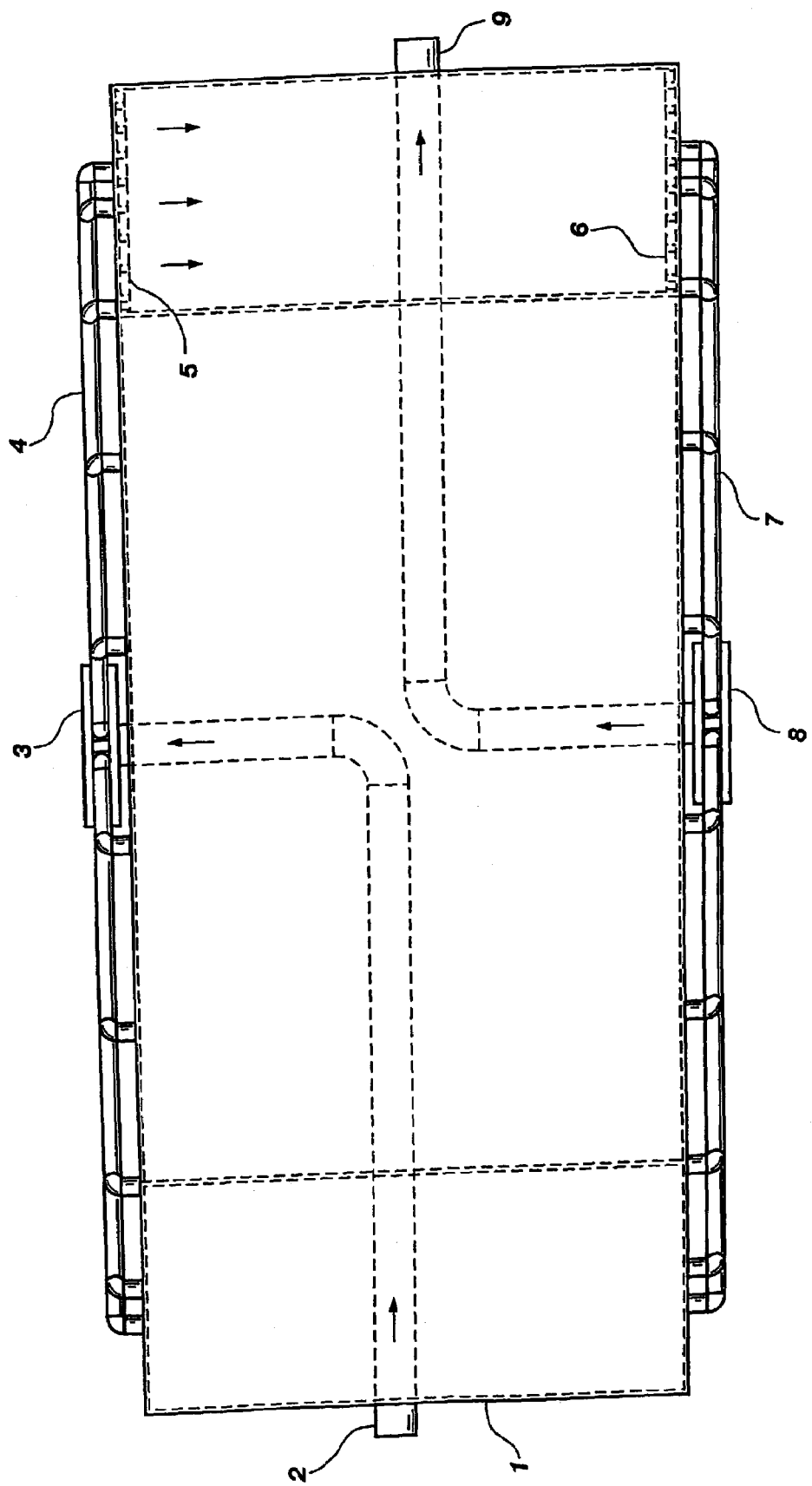
FIG. 1 is a side elevation of the present invention, showing internal components in shadow.

With reference to the appended drawings, the improved vessel of the present invention will now be described. Specifically referring to FIGS. 1 and 2, the improved vessel body 1 is toroidal. Ideally this toroidal shape is based on a rectangle rotated about a rotational axis, said rectangle being in a same plane as, but not being intersected by, the axis. The toroidal shape incorporates the pressure containment advantages inherent with a cylindrical shape and allows collection and distribution systems to be located axially in the void within the toroid. This positioning allows for more efficient and uniform distribution and collection of fluids, as a single distribution plenum 3 and a single collection plenum 8 are required. Toroidal body 1 also has two circumferential walls 10, 11 as opposed to one, as with a cylinder. The inner wall 11 provides additional support to the toroidal body 1 as compared to a cylinder.

Figure 2:
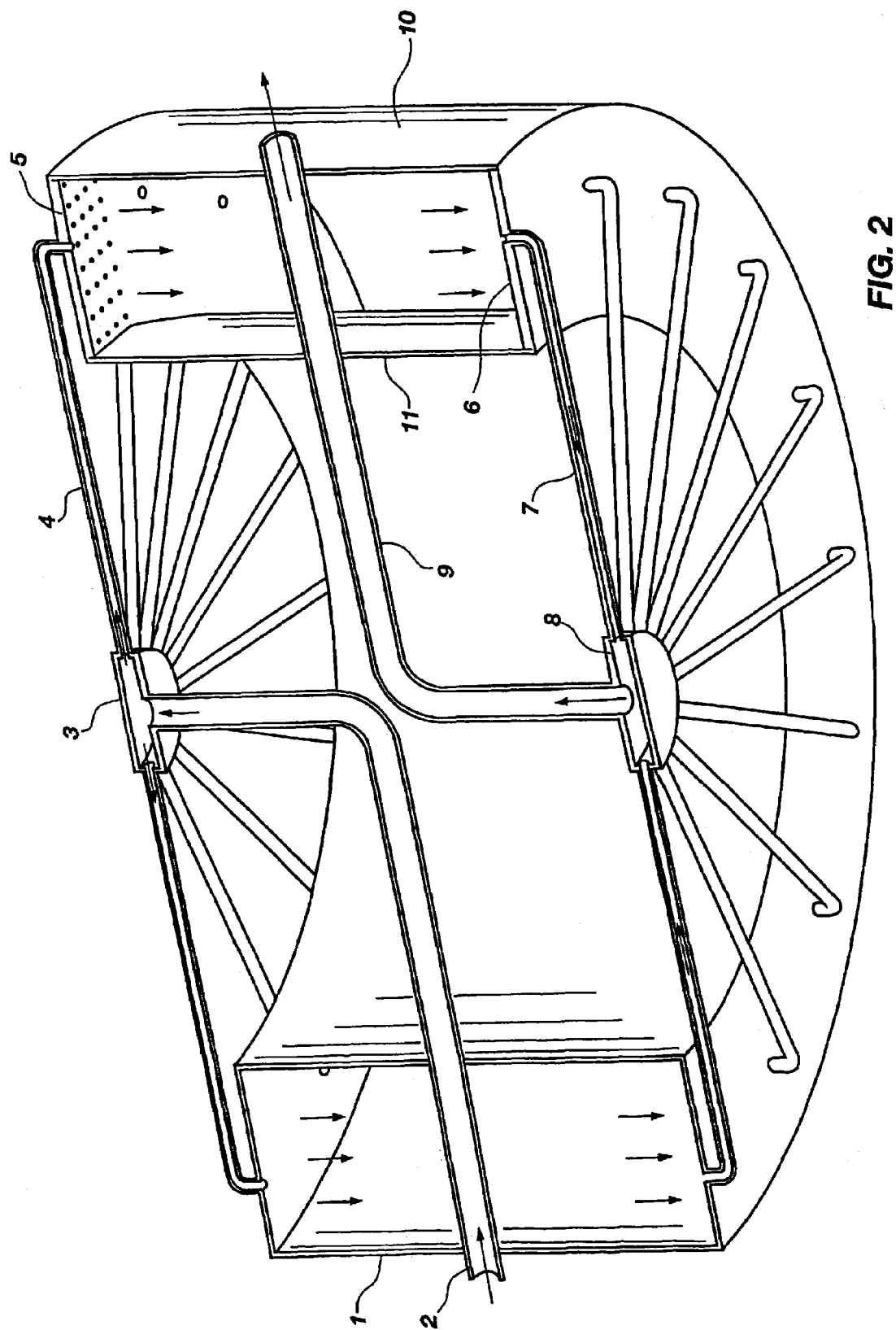
FIG. 2 is a perspective view of half of the invention taken along a vertical cross-section, with arrows depicting fluid flow.
Figure 4:
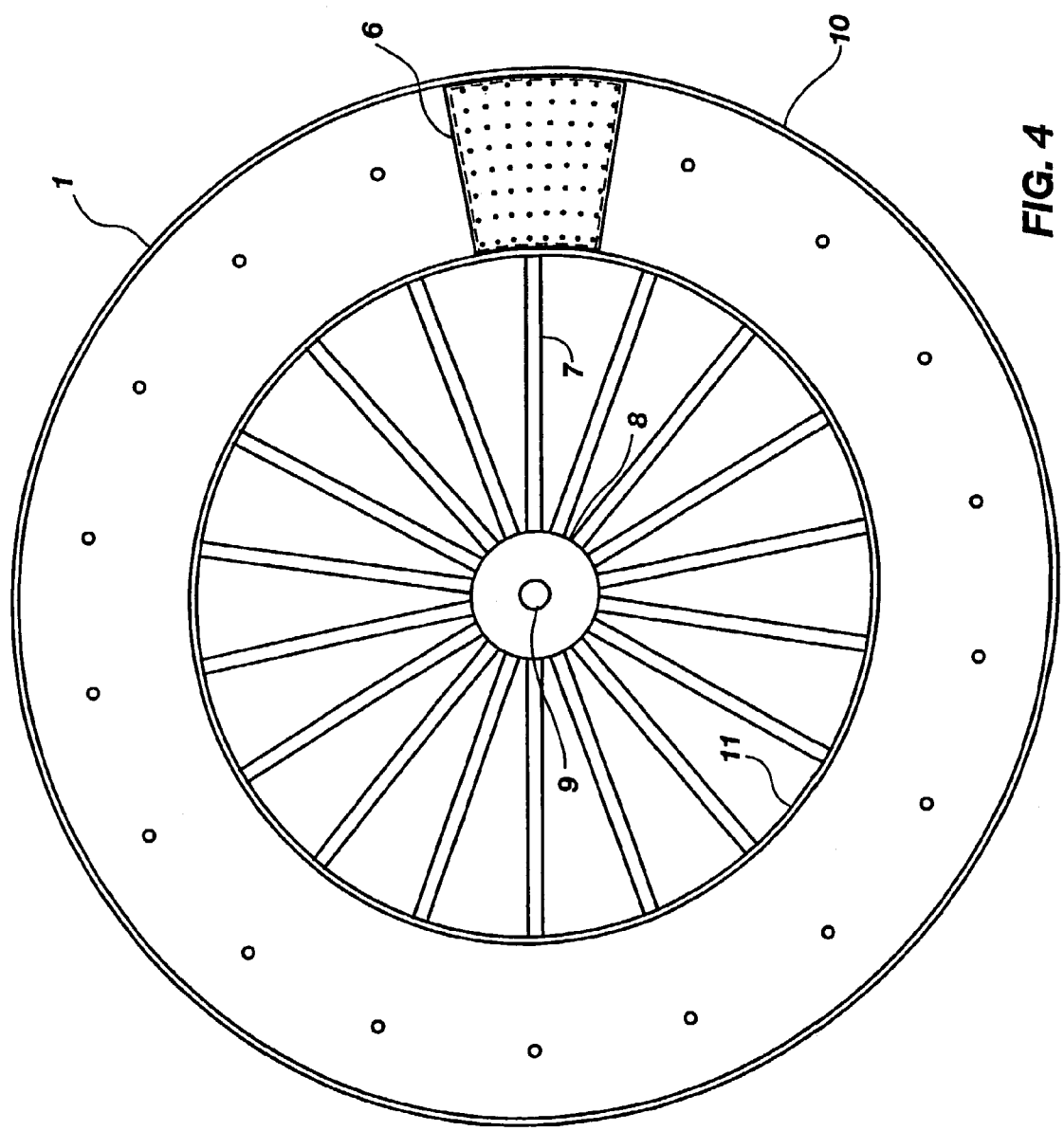
FIG. 4 is a horizontal cross-section of the present invention.

The toroidal vessel allows for a centrally located collection/distribution system. One such system is shown in the appended figures. Referring to FIG. 2, an intake conduit 2 enters the void through inner and outer body walls 11, 10 and makes a right-angled turn along the rotational axis of the toroidal body 1. At a location approximate to the upper plane of the toroidal body 1, conduit 2 interfaces distribution plenum 3. Plenum 3 is located so that the plenum's normal axis is coaxial to the rotational axis of toroidal body 1. Plenum 3 has a plurality of outlets, each connected to a distribution conduit 4. Conduits 4 all have an identical hydraulic path and are symmetrical relative to the normal axis of the plenum 3. Each distribution conduit interfaces the toroidal body 1 at a distribution element 5. The distribution elements 5, shown in FIG. 5 are all in a planar relation to the top of the toroidal body 1. A collection system is similarly constructed and oppositely oriented, Shown in FIG. 4, with collection elements 6 planar with the bottom of the toroidal body 1, a plurality of collection conduits 7, a collection plenum 8, and an outflow conduit 9.

Figure 3:
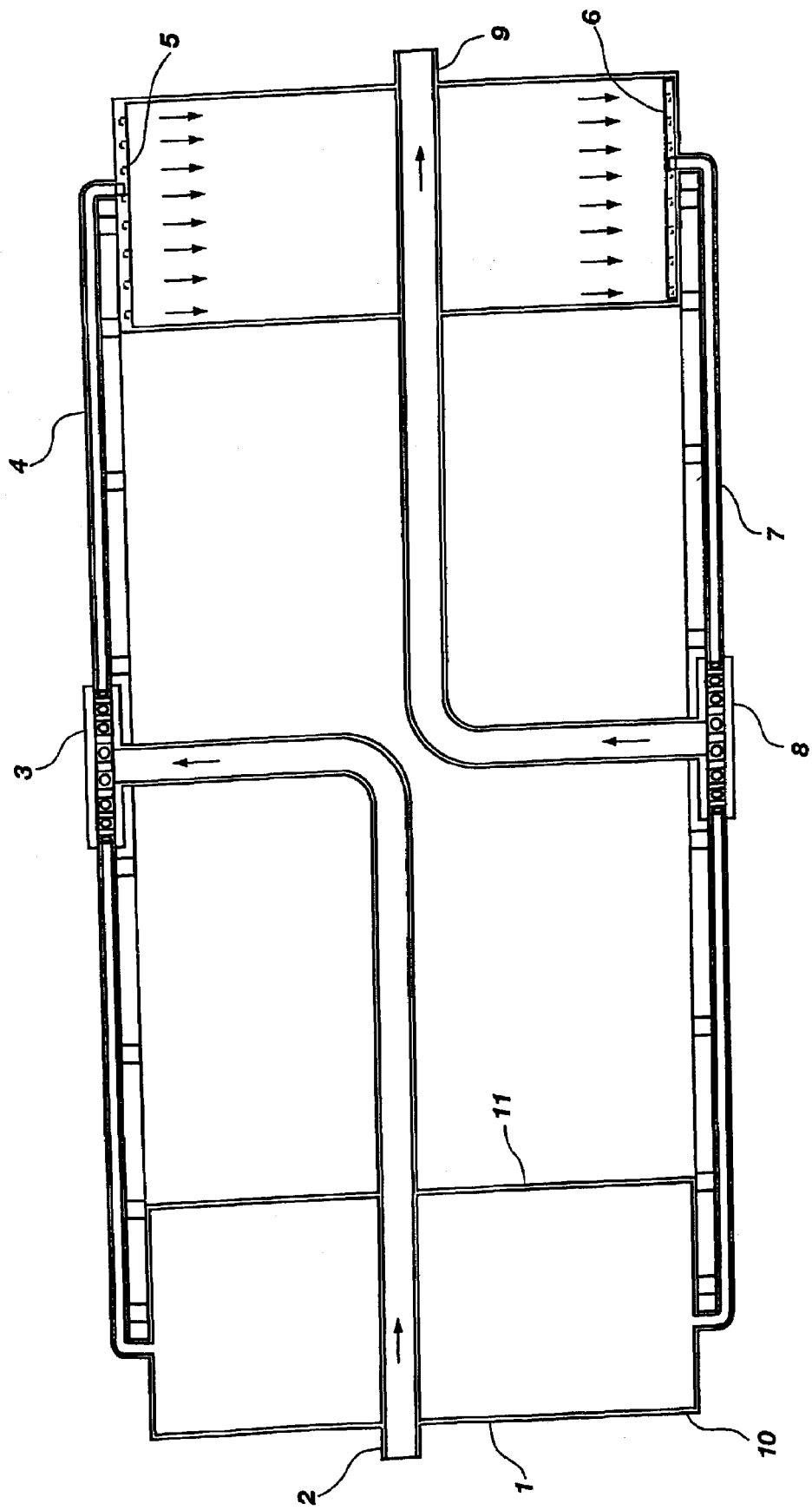
FIG. 3 is a vertical cross-section of the present invention.

FIG. 3 depicts the flow of liquid through the improved system. Fluid enters the distribution manifold through intake conduit 2 and into distribution plenum 3. From plenum 3, fluid disperses through distribution conduits 4 and into toroidal body 1 via flat dispersion elements 5. The symmetrical construction of this system provides uniform distribution of the fluid with a much simpler construction. Fluid passes down, through toroidal body 1, interacting with a contained medium and is collected by collection elements 6. Fluid then passes through the collection manifold in a manner similar to distribution.

The symmetrical distribution advantages afforded by the toroidal vessel design can be retrofitted within conventional cylindrical vessels by inserting an inner cylinder.

Though the disclosure presents a best mode for practicing the invention and an associated manifold system, it is to be understood that numerous variations may be made to the above-disclosed embodiment and still practice the present invention. It is, therefore to be understood that the invention defined by the appended claims is not to be limited by particular details set forth in the above description.

What is claimed is:

1. A vessel and manifold system for uniform plug-flow fluid distribution applications, the system comprising:
    an enclosed toroidal vessel body having planar top and a planar bottom, and a rotational axis, located within a central void of the toroidal vessel and perpendicular to a horizontal cross-sectional plane of the vessel body;
    an improved intake manifold further comprising:
        a fluid intake conduit;
        a distribution plenum, in fluid communication with the intake conduit and located at the rotational axis of the toroidal vessel;
        a plurality of radial distribution conduits, each one in fluid communication with the intake plenum at one of a plurality of outlets and all conduits having identical hydraulic paths; and
    a plurality of planar distributor elements, located within the top of the toroidal vessel body, coplanar with said top of said vessel body and each element in fluid communication with one distribution conduit; and
    an improved collection manifold, comprised of components similar to the distribution manifold with planar collection elements located within the bottom of the toroidal vessel body, a plurality of collection conduits, a collection plenum and an outflow conduit, with the collection components correspondingly opposite to the components of the intake manifold but in identical relation to each other as the corresponding components of the intake manifold, said planar collection elements being positioned coplanar with said bottom of said toroidal vessel body;
    wherein, a fluid is passed from the fluid intake conduit into the intake plenum and is evenly disbursed along the distribution conduits to the distribution elements into the vessel body, interacting with and passing through a medium contained within the vessel body, being thereafter collected by the collection elements, passed through to the collection conduits and collection plenum and out of the system through the outflow conduit.

2. The vessel and manifold system of claim 1, wherein the vessel is a rectangular toroid, having a flat top and a flat bottom.

3. The vessel and manifold system of claim 1 wherein the distribution system is a fractal structure.

4. The vessel and manifold system of claim 1 wherein the collection system is a fractal structure.

5. The vessel and manifold system of claim 3 wherein said collection system is a fractal system.

* * * * *